United States Patent [19]

Nishiyama et al.

[11] 4,347,390

[45] Aug. 31, 1982

[54] PROCESS FOR PRODUCING 1-BROMO-3,5-DICHLOROBENZENE

[75] Inventors: Ryuzo Nishiyama, Takatsuki; Kanichi Fujikawa, Kyoto; Isao Yokomichi, Kusatsu; Yasuhiro Tsujii, Kusatsu; Itaru Shigehara, Kusatsu; Kuniaki Nagatani, Kusatsu; Shigeyuki Nishimura, Shiga, all of Japan

[73] Assignee: Ishihara Sangyo Kaisha Ltd., Osaka

[21] Appl. No.: 206,392

[22] Filed: Nov. 13, 1980

Related U.S. Application Data

[63] Continuation of Ser. No. 823,098, Aug. 9, 1977, abandoned.

[30] Foreign Application Priority Data

| Aug. 25, 1976 | [JP] | Japan | 51-100504 |
| Sep. 9, 1976 | [JP] | Japan | 51-108518 |
| Oct. 12, 1976 | [JP] | Japan | 51-122591 |
| Oct. 12, 1976 | [JP] | Japan | 51-122592 |

[51] Int. Cl.$^3$ ............................................. C07C 17/02
[52] U.S. Cl. ................................................... 570/202
[58] Field of Search ................................................... 570/202

[56] References Cited

U.S. PATENT DOCUMENTS

| 2,666,085 | 1/1954 | Fitzpatrick | 260/650 R |
| 2,866,829 | 12/1958 | Woodruff | 260/650 R |
| 3,345,423 | 10/1967 | Tolgyesi | 260/650 R |
| 3,833,674 | 9/1974 | Brackenridge | 260/650 R |
| 3,965,197 | 6/1976 | Stepniczka | 260/650 R |

FOREIGN PATENT DOCUMENTS 1256255  1/1963  France ............................ 260/650 R

OTHER PUBLICATIONS

Beman, J. Org. Chem. 27 (1962) pp. 3690-3692.

*Primary Examiner*—Arthur P. Demers
*Attorney, Agent, or Firm*—Oblon, Fisher, Spivak, McClelland & Maier

[57] ABSTRACT

1-Bromo-3,5-dichlorobenzene is produced in high efficiency by a special isomerization of monobromodichlorobenzene in the presence of an aluminum halide and separating the object product and recycling a residue.

1-Bromo-3,5-dichlorobenzene is useful intermediates for various agricultural chemicals, dyes and medicines.

8 Claims, No Drawings

PROCESS FOR PRODUCING 1-BROMO-3,5-DICHLOROBENZENE

This is a continuation of application Ser. No. 823,098, filed Aug. 9, 1977, now abandoned.

BACKGROUND OF THE INVENTION

The present invention relates to a process for producing 1-bromo-3,5-dichlorobenzene which is remarkably advantageous in the industrial operation.

The 1-substituted-3,5-dichlorobenzenes such as 3,5-dichlorophenol, 3,5-dichlorothiophenol, 1-alkoxy-3,5-dichlorobenzene, 3,5-dichloroaniline, and 3,5-dichlorobenzonitrile are useful intermediates for agricultural chemicals, medicines and dyes and a large amount of consumption is expected.

The inventors have considered that these 1-substituted-3,5-dichlorobenzenes are advantageously obtained from 1-bromo-3,5-dichlorobenzene in an industrial operation and have studied the process for producing 1-bromo-3,5-dichlorobenzene. As the results, the process for producing 1-bromo-3,5-dichlorobenzene by a special isomerization has been completed.

The isomerizations of halobenzenes have been studied and disclosed in U.S. Pat. No. 2,666,085 and The Journal of Organic Chemistry Vol. 27, 3690-3692 (1962) wherein dichlorobenzene or bromochlorobenzene is isomerized in the presence of an aluminum halide.

However, it has not known that 1-bromo-3,5-dichlorobenzene is produced by an isomerization of monobromodichlorobenzene.

SUMMARY OF THE INVENTION

It is an object of the present invention to provide a novel process for producing 1-bromo-3,5-dichlorobenzene.

It is another object of the present invention to provide a process for producing 1-bromo-3,5-dichlorobenzene having high purity with industrial advantages.

The other objects of the present invention will be apparent from the following descriptions.

The foregoing objects of the present invention have been attained by producing 1-bromo-3,5-dichlorobenzene by a special isomerization of monobromodichlorobenzene with or without dichlorobenzenes and dibromodichlorobenzenes in the presence of an aluminum halide at a mole ratio of 0.02 to 1 to total of halobenzenes (monobromodichlorobenzenes, dichlorobenzenes, dibromodichlorobenzenes) at 80° to 180° C.; and a separation of 1-bromo-3,5-dichlorobenzene from the reaction mixture and a recycling of a residue to the special isomerization step.

DETAILED DESCRIPTION OF THE PREFERRED EMBODIMENTS

The present invention has been completed by the following findings.

(1) 1-Bromo-3,5-dichlorobenzene can be effectively produced with industrial advantages by utilizing the special isomerization of one or more monobromodichlorobenzenes.

(2) The reaction mixture obtained by the special isomerization includes the object compound of 1-bromo-3,5-dichlorobenzene and the isomers and other halobenzenes such as dichlorobenzenes, dibromodichlorobenzenes, 1-Bromo-3,5-dichlorobenzene having high purity can be easily separated by a simple method such as a crystallization or a combination of a distillation and a crystallization.

(3) Even though the residue obtained by separating 1-bromo-3,5-dichlorobenzene from the reaction mixture is recycled to use it with a new raw material in the special isomerization, the object product could be obtained at the similar ratio to those of the cases using only the raw material.

(4) The facts in (2) and (3) well fit to the recycling step. By the consideration of the recycling step, the industrial operation can be attained in high yield.

The advantages of the present invention are as follows.

(1) The special isomerization can be attained in relatively mild conditions.

(2) The separation of 1-bromo-3,5-dichlorobenzene from the reaction mixture can be easily carried out so as to obtain 1-bromo-3,5-dichlorobenzene having high purity in high yield.

(3) The residue obtained by separating 1-bromo-3,5-dichlorobenzene from the reaction mixture can be recycled completely without separating by-products out of the system, whereby the object compound can be obtained in high yield.

(4) The resulting 1-bromo-3,5-dichlorobenzene can be easily converted into 3,5-dichlorophenol, 3,5-dichlorothiophenol, 1-alkoxy-3,5-dichlorobenzene, 3,5-dichloroaniline, 3,5-dichlorobenzonitrile etc. In accordance with the conversions from 1-bromo-3,5-dichlorobenzene, there are various industrial advantages such as less steps and less waste water in comparison with conventional processes.

The process of the present invention will be described in detail.

The special isomerization is carried out by charging an aluminum halide into a fresh monobromodichlorobenzene or a mixture of a fresh monobromodichlorobenzene and the recycled residue after the separation, and heating the mixture under stirring.

The aluminum halides include anhydrous aluminum chloride, anhydrous aluminum bromide and a mixture thereof. The anhydrous aluminum chloride is economically advantageous. The aluminum halides can be ones having the quality of commercially available industrial raw material.

The aluminum halide is added at a mole ratio of 0.02 to 1 preferably 0.1 to 0.5 to total the amount of halobenzenes (monobromodichlorobenzenes, dichlorobenzenes and dibromodichlorobenzenes) though it is not critical and it depends upon differences in the reaction conditions.

The special isomerization is carried out at 80° to 180° C., preferably 120° to 170° C. for 0.5 to 50 hours.

When the reaction temperature is too high or too low, the special isomerization can not be attained in the optimum condition from the viewpoints of the reaction time, the yield of the object compound, and the production of by-products which should be separated to taken out of the system.

In the special isomerization, disproportionation occurs simultaneously so that a reaction mixture is attained which contains dichlorobenzenes and dibromodichlorobenzenes. That is, the reaction mixture comprises the object compound of 1-bromo-3,5-dichlorobenzene and the other halobenzenes such as o-, m- and p-dichlorobenzenes; monobromodichlorobenzenes e.g. 1-bromo-2,4-dichlorobenzene, 1-bromo-2,5-dichlorobenzene, 1-bromo-3,4-dichlorobenzene, and dibromodichlorobenzenes, e.g., 1,5-dibromo-2,4-dichlorobenzene, 1,4-dibromo-2,5-dichlorobenzene, 1,2-dibromo-4,5-dichlorobenzene etc.

The amounts of (i) the object compound of 1-bromo-3,5-dichlorobenzene; (ii) the other monobromodichlorobenzenes, (iii) the dichlorobenzenes and (iv) the dibromodichlorobenzenes are respectively (i) about 15 to 50wt. %; (ii) about 15 to 50 wt. %; (iii) about 10 to 40 wt. % and (iv) a trace to about 30 wt. %.

The reaction mixture is usually cooled and then it is washed in water or a dilute hydrochloric acid and the resulting oily product is cooled to room temperature or lower whereby 1-bromo-3,5-dichlorobenzene is crystallized.

The crystallized material is filtered to obtain solid product of 1-bromo-3,5-dichlorobenzene.

The filtrate contains a small amount of non-separated 1-bromo-3,5-dichlorobenzene, other monobromodichlorobenzenes, dichlorobenzenes and dibromodichlorobenzenes. The filtrate is recycled to the special isomerization step. The yield of 1-bromo-3,5-dichlorobenzene can be increased by distilling the reaction mixture before the crystallization to collect the main distillate of monobromodichlorobenzenes and then, crystallizing it.

When the reaction mixture contains a large amount of dibromodichlorobenzenes, it is preferable to separate 1-bromo-3,5-dichlorobenzene of high purity by the combination of the distillation and the crystallization.

The formation of dibromodichlorobenzenes can be retarded by having a suitable amount of dichlorobenzene present during the special isomerization. This is advantageous in the industrial operation.

About 10 to 35 wt. % of the reaction mixture in the special isomerization is usually separated as the object compound. All of the raw materials of monobromodichlorobenzenes may be substantially converted to 1-bromo-3,5-dichlorobenzene by recycling the residue obtained by the separation from the reaction mixture.

When 1-bromo-2,4-dichlorobenzene is used as the raw material of monobromodichlorobenzene, the special isomerization of the present invention can be smoothly performed. In this case, the special isomerization can be attained in relatively mild conditions such at 80° to 170° C. preferably 120° to 150° C. for 0.5 to 10 hours under the atmospheric pressure.

The reaction mixture in the special isomerization contains about 35 to 50 wt. % of 1-bromo-3,5-dichlorobenzene and accordingly, the yield of 1-bromo-3,5-dichlorobenzene is relatively high.

1-Bromo-2,5-dichlorobenzene or a mixture of 1-bromo-2,5-dichlorobenzene and 1-bromo-2,4-dichlorobenzene can be effectively used. When a mixture containing more than 20 wt. % of 1-bromo-3,4-dichlorobenzene is used, the yield of the object compound in the special isomerization is not so high whereby it is disadvantageous in the industrial operation in comparison with the cases using suitable raw materials.

Said monobromodichlorobenzenes can be easily obtained as follows.

The o-, m- or p-dichlorobenzenes or mixture thereof which is used as intermediates for syntheses of various organic compounds is brominated at 0° to 100° C. in the presence of aluminum chloride, ferric chloride or iron powder. The bromobenzene is chlorinated in the same condition. The dichlorobenzene is reacted with the dibromodichlorobenzene in the presence of an aluminum halide for 1 to 5 hours. In these methods, 1-bromo-2,4-dichlorobenzene, 1-bromo-2,5-dichlorobenzene, and 1-bromo-3,4-dichlorobenzene etc. can be obtained in high yield.

The monobromodichlorobenzenes having suitable composition for the special isomerization can be obtained by selecting suitable raw materials, selecting suitable reaction condition, or separating or purifying the reaction product.

In the other embodiments of the present invention, dichlorobenzenes are used as the starting material and the production of monobromodichlorobenzene by a bromination and the production of 1-bromo-3,5-dichlorobenzene by the special isomerization of the monobromodichlorobenzene are combined in parallel or in sequence.

The process comprises the following steps.

(1) The dichlorobenzene is brominated by adding bromine at 0° to 180° C. in the presence of an aluminum halide at a mole ratio of 0.001 to 1 to total of halobenzenes (monobromodichlorobenzenes, dichlorobenzenes and dibromodichlorobenzenes).

(2) The special isomerization of the resulting monobromodichlorobenzenes is performed at 80° to 180° C. in the presence of an aluminum halide at a mole ratio of 0.02 to 1 to total of halobenzenes (monobromodichlorobenzenes, dichlorobenzenes and dibromodichlorobenzenes).

(3) The resulting 1-bromo-3,5-dichlorobenzene is separated from the reaction mixture.

(4) The residue (containing monobromodichlorobenzenes, dichlorobenzenes and dibromodichlorobenzenes) is recycled to the step (1) or (2).

The step (2) is carried out in parallel to the step (1) or in sequential to the step (1).

The process is carried out as follows in detail.

(1) Bromine is added to dichlorobenzene with or without the recycling materials at 0° to 80° C. preferably 0° to 70° C. in the presence of an aluminum halide at a mole ratio of 0.001 to 0.1 preferably 0.005 to 0.1 to total of halobenzenes (monobromodichlorobenzene, dichlorobenzene and dibromodichlorobenzene). After the addition of bromine, an aluminum halide is further added so as to give a mole ratio of 0.02 to 1 preferably 0.1 to 0.5 total of halobenzenes (monobromodichlorobenzene, dichlorobenzene and dibromodichlorobenzene) and the mixture is heated to the temperature for the special isomerization of 80° to 180° C. preferably 120° to 170° C. whereby the special isomerization is performed sequentially to the bromination.

(2) Bromine is added to dichlorobenzene with or without the recycling materials at 0° to 80° C. preferably 0° to 70° C. in the presence of an aluminum halide at a mole ratio of 0.02 to 1 preferably 0.1 to 0.5 to total of halobenzenes (monobromodichlorobenzene, dichlorobenzene and dibromodichlorobenzene). After the addition of bromine, the mixture is heated to the temperature for the special isomerization of 80° to 180° C. preferably 120° to 170° C. whereby the special isomerization is performed substantially sequentially to the bromination.

(3) Bromine is added to dichlorobenzene with or without the recycling materials in the presence of aluminum halide at a mole ratio of 0.02 to 1 preferably 0.1 to 0.5 to total of halobenzenes (monobromodichlorobenzene, dichlorobenzene, and dibromodichlorobenzene) and the reaction temperature is raised to 80° to 180° C. preferably 120° to 170° C. before or during the addition of bromine whereby the special isomerization is performed together with the bromination.

In these cases, a residue obtained by separating 1-bromo-3,5-dichlorobenzene from the reaction mixture can be added to the system before the initiation of the addition of bromine or the special isomerization as the recycling materials. The residue can be added at the other time as far as enough time for the special isomerization is given.

In the bromination, an aluminum halide is added to dichlorobenzene or a mixture of dichlorobenzene and the residue as the recycling material and bromine is added while the mixture is stirred whereby the bromination of dichlorobenzene is performed. The amount of the aluminum halide is usually more than 0.001 mole preferably more than 0.005 mole per 1 mole of halobenzenes.

The aluminum halides used for the bromination can be the same with the aluminum halides used in the special isomerization, and have catalytic activity to both of the bromination and the special isomerization. The amount of the aluminum halide needed for the special isomerization can be also added in the step of bromination, the amount of the aluminum halide for the bromination such as 0.001 to 0.1 mole per 1 mole of halobenzenes can be also added in the step of the bromination and the aluminum halide can be added to give the amount for the special isomerization such as 0.02 to 1 mole per 1 mole of halobenzenes in the step of the special isomerization.

The temperature for the bromination is usually 0° to 80° C. preferably 0° to 70° C. When the bromination is performed with the special isomerization, the temperature is usually 80° to 180° C. preferably 120° to 170° C., and the reaction time is usually 0.5 to 50 hours.

When the amount of bromine is more than stoichiometric amount (equimole) to the newly added dichlorobenzene in the bromination, the amounts of dibromodichlorobenzenes such as 1,5-dibromo-2,4-dichlorobenzene, 1,4-dibromo-2,5-dichlorobenzene, 1,2-dibromo-4,5-dichlorobenzene are increased to cause serious disadvantages in the industrial operation.

When metadichlorobenzene is used as the starting material of dichlorobenzene, the bromination and the special isomerization can be smoothly performed.

In this case, the reaction time for the bromination and isomerization is usually in a range of 0.5 to 15 hours. In the reaction mixture obtained by the special isomerization, about 35 to 50 wt. % of the object compound of 1-bromo-3,5-dichlorobenzene is included, and accordingly, the yield 1-bromo-3,5-dichlorobenzene is relatively high.

As it is clear from below-mentioned examples, paradichlorobenzene or a mixture of paradichlorobenzene and metadichlorobenzene is also suitable as the starting material. However when the starting material contains more than 20 wt. % of orthodichlorobenzene. The yield of the object compound in the special isomerization is relatively small to be disadvantageous in the industrial operation in comparison with the cases using suitable starting material.

The object compound of 1-bromo-3,5-dichlorobenzene obtained in the process of the present invention is useful in the synthetic chemical industries and it can be converted to various compounds. Especially, it can be easily converted to desired compounds by substitutions of bromine atom in the reactions with nucleophilic reagents. For example, 3,5-dichloroaniline can be obtained in high yield by reacting 1-bromo-3,5-dichlorobenzene with ammonia water in the presence of cuprous chloride at the elevated temperature under high pressure.

The present invention will be further illustrated by certain examples.

EXAMPLE 1

Production of 1-bromo-3,5-dichlorobenzene from other monobromodichlorobenzenes

In a four necked flask equipped with a stirrer, a thermometer and reflux condenser, monobromodichlorobenzene and an anhydrous aluminum halide were charged and the special isomerization was carried out by heating the mixture with stirring under the conditions shown in Tables 1-1 and 1-2.

The reaction mixture was cooled and was poured into water and was washed with water to obtain a crude oily product.

According to the gas chromatographic analysis of the crude oily product, the results shown in Tables 1-1 and 1-2 were found. The crude oily product contained the object compound of 1-bromo-3,5-dichlorobenzene and other monobromodichlorobenzenes such as 1-bromo-2,4-dichlorobenzene, 1-bromo-2,5-dichlorobenzene, 1-bromo-3,4-dichlorobenzene, 1-bromo-2,3-dichlorobenzene, and 1-bromo-2,6-dichlorobenzene (referred to as MBCB) and dichlorobenzenes (referred to as DCB) and dibromodichlorobenzenes (referred to as DBCB).

The crude oily product was distilled at 130° to 137° C. under a reduced pressure of 60 mm Hg to separate the main distillate (mainly including monochlorobenzenes). The main distillate was cooled to room temperature or lower to crystalize the object compound. The crystallized product was filtered to obtain solid of 1-bromo-3,5-dichlorobenzene having a purity of higher than 95%.

The filtrate contained main components of other monobromodichlorobenzenes with a small amount of 1-bromo-3,5-dichlorobenzene which was not separated.

In the distillation, the initial distillate mainly contained dichlorobenzenes with a small amount of water which was not separated, and the last distillate mainly contained dibromodichlorobenzenes.

The results of the first isomerization are shown in Table 1-1.

The residue of the filtrate, the initial distillate and the last distillate was recycled to mix with the fresh raw material and the second isomerization was carried out, and the operation was repeated.

The results of the isomerization in the steady state are shown in Table 1-2.

TABLE 1-1

| | First isomerization | |
|---|---|---|
| Test No. | 1 | 2 |
| Raw material MBCB | | |
| Cl sites | 2,5-Cl$_2$ | 2,4-Cl$_2$ |
| Amount (g) | 100 | 100 |
| Condition of isomerization | | |
| Type of Al halide | AlBr$_3$ | AlCl$_3$ |
| Amount (g) | 50 | 30 |
| Temperature (°C.) | 160–170 | 140–150 |
| Time (hr.) | 8 | 4 |
| Crude oily product | | |
| Amount (g) | 94 | 99 |
| Formula (weight %) | | |
| Object comp. | 30 | 45 |
| DCB | 14 | 10 |
| MBCB | 32 | 25 |
| DBCB | 24 | 20 |

TABLE 1-1-continued

| | First isomerization | |
|---|---|---|
| Test No. | 1 | 2 |
| Initial distillate (g) | 13 | 10 |
| Main distillate (g) | | |
| object compound | 20 | 38 |
| filtrate | 37 | 30 |
| Last distillate (g) | 20 | 17 |

TABLE 1-2

| | Isomerization in steady state | |
|---|---|---|
| Test No. | 1 | 2 |
| Raw material MBCB | | |
| Cl sites | 2,5-Cl$_2$ | 2,5-Cl$_2$ |
| Amount (g) | 30 | 43 |
| Recycling material (g) | 70 | 57 |
| Condition of isomerization | | |
| Type of Al halide | AlBr$_3$ | AlCl$_3$ |
| Amount (g) | 50 | 30 |
| Temperature (°C.) | 160–170 | 140–150 |
| Time (hr.) | 6 | 4 |
| Crude oily product | | |
| Amount (g) | 96 | 98 |
| Formula (weight %) | | |
| object comp. | 30 | 44 |
| DCB | 13 | 11 |
| MBCB | 34 | 26 |
| DBCB | 27 | 19 |
| Initial distillate (g) | 14 | 11 |
| Main distillate (g) | | |
| object compound | 21 | 35 |
| filtrate | 39 | 32 |
| Last distillate (g) | 20 | 18 |

EXAMPLE 2

Production of 1-bromo-3,5-dichlorobenzene from other monobromodichlorobenzenes

The first isomerization of Example 1 was repeated except adding dichlorobenzene. The results are shown in Table 2-1.

The second isomerization of Example 1 was repeated except that a part or all of the residue obtained by separating the object compound from the crude oily product obtained by the first isomerization was recycled. The results are shown in Table 2-2.

TABLE 2-1

| | First isomerization | | | | |
|---|---|---|---|---|---|
| Test No. | 3 | 4 | 5 | 6 | 7 |
| Raw material MBCB | | | | | |
| Cl sites 3,4-Cl$_2$ | — | — | 150 | 20 | — |
| Amount (g) 2,4-Cl$_2$ | 300 | 300 | — | 120 | 300 |
| 2,5-Cl$_2$ | — | — | 50 | 60 | — |
| Condition of isomerization | | | | | |
| Al halide | | | | | |
| Type | AlCl$_3$ | AlCl$_3$ | AlCl$_3$ | AlCl$_3$ | AlCl$_3$ |
| Amount (g) | 200 | 60 | 90 | 80 | 70 |
| DCB | | | | | |
| Cl site o- | — | — | 97.5 | 20 | — |
| Amount (g) m- | 300 | 300 | — | 120 | 50 |
| p- | — | — | 32.5 | 60 | — |
| Temperature (°C.) | 140 | 140 | 170 | 160 | 140 |
| Time (hr) | 4 | 6 | 30 | 10 | 4 |
| Crude oily product | | | | | |
| Amount (g) | 595 | 591 | 315 | 383 | 347 |
| Formula (weight %) | | | | | |
| Object comp. | 33 | 33 | 27 | 25 | 45 |
| DCB | 50 | 50 | 38 | 50 | 20 |
| MBCB | 17 | 17 | 33 | 25 | 25 |
| DBCB | tr. | tr. | 2 | tr. | 10 |
| Initial distillate (g) | 298 | 295 | 120 | 195 | 70 |
| Main distillate | | | | | |
| Object compound (g) | 142 | 141 | 40 | 57 | 97 |
| filtrate (g) | 155 | 154 | 145 | 130 | 142 |
| Last distillate (g) | — | — | — | — | 30 |

TABLE 2-2

| | Second isomerization | | | | |
|---|---|---|---|---|---|
| Test No. | 3 | 4 | 5 | 6 | 7 |
| Raw material MBCB | | | | | |
| Cl sites 3,4-Cl$_2$ | — | — | 41 | 7 | — |
| Amount (g) 2,4-Cl$_2$ | 50 | 50 | — | 42 | 50 |
| 2,5-Cl$_2$ | — | — | 14 | 21 | — |
| Recycling material | | | | | |
| Type | Ⓐ 50 | Ⓐ 50 | Ⓑ 265 | Ⓑ 325 | Ⓐ 50 |
| Condition of isomerization | | | | | |
| Al halide | | | | | |
| Type | AlCl$_3$ | AlCl$_3$ | AlCl$_3$ | AlCl$_3$ | AlCl$_3$ |
| Amount (g) | 60 | 20 | 60 | 40 | 25 |
| DCB | | | | | |
| Cl sites o- | — | — | 7.5 | 0.5 | — |
| Amount (g) m- | 100 | 100 | — | 3 | 17 |
| p- | — | — | 2.5 | 1.5 | — |
| Temperature (°C.) | 140 | 140 | 170 | 160 | 140 |
| Time (hr.) | 4 | 8 | 20 | 10 | 4 |
| Crude oily product | | | | | |
| Amount (g) | 192 | 192 | 323 | 385 | 115 |
| Formula (weight %) | | | | | |
| Object comp. | 33 | 33 | 28 | 25 | 44 |
| DCB | 50 | 50 | 38 | 50 | 20 |
| MBCB | 17 | 17 | 32 | 25 | 26 |
| DBCB | tr. | tr. | 2 | tr. | 10 |
| Initial distillate (g) | 100 | 97 | 122 | 196 | 23 |
| Main distillate | | | | | |
| Object compound (g) | 47 | 45 | 45 | 58 | 30 |
| filtrate (g) | 52 | 49 | 147 | 129 | 51 |
| Last distillate (g) | — | — | — | — | 10 |

Note:
tr.: trace
Ⓐ : a part of filtrate
Ⓑ : a whole of initial distillate and filtrate

EXAMPLE 3

Production of 1-bromo-3,5-dichlorobenzene from dichlorobenzene

In a four necked flask equipped with a stirrer, a thermometer and a refluxing condenser, dichlorobenzene and anhydrous aluminum halide were charged and bromine was added dropwise to the mixture from a dropping funnel with stirring under conditions shown in Tables 3-1 and 3-2.

After the addition of bromine, an additional aluminum halide was added and the mixture was heated to perform the special isomerization.

After cooling the reaction mixture, the reaction mixture was poured into water and was washed with water to obtain a crude oily product.

According to the gas chromatographic analysis of the crude oily product, the following results are found.

The crude oily product contained the object compound of 1-bromo-3,5-dichlorobenzene with the other monobromodichlorobenzenes such as 1-bromo-2,4-dichlorobenzene, 1-bromo-2,5-dichlorobenzene, 1-bromo-3,4-dichlorobenzene, 1-bromo-2,3-dichlorobenzene and 1-bromo-2,6-dichlorobenzene (referring to as MBCB) and dichlorobenzenes (referring to as DCB) and dibromodichlorobenzenes (referring to as DBCB).

The crude oily product was distilled at 130° to 137° C. under a reduced pressure of 60 mmHg to separate the main distillate. The main distillate was cooled to the room temperature or lower to crystalize the object compound. The crystallized product was filtered to obtain solid of 1-bromo-3,5-dichlorobenzene having a purity of higher than 95%.

The filtrate contained main components of other monobromodichlorobenzenes with a small amount of 1-bromo-3,5-dichlorobenzene which was not separated.

In the distillation, the initial distillate and the last distillate respectively contained main components of dichlorobenzenes and dibromodichlorobenzenes.

The results of the first isomerization are shown in Table 3-1.

The whole of the residue of the filtrate, the initial distillate and the last distillate was recycled to mix with the fresh raw material and the second isomerization was carried out and the operation was repeated. The results of the isomerization in the steady state are shown in Table 3-2.

TABLE 3-1

| | First Reaction | | | |
|---|---|---|---|---|
| Test No. | 8 | 9 | 10 | 11 |
| Raw material DCB | | | | |
| Cl site     m- | — | 100 | 40 | 257 |
| Amount (g)  p- | 100 | — | 160 | 110 |
| Al halide | | | | |
| Type | AlCl$_3$ | AlCl$_3$ | AlCl$_3$ | AlCl$_3$ |
| Initial amount (g) | 4 | 4 | 8 | 10 |
| + | + | + | + | + |
| Additional amount (g) | 20 | 20 | 50 | 80 |
| Condition of Reaction | | | | |
| Br addition | | | | |
| Amount (g) | 87 | 87 | 174 | 320 |
| Time (hr.) | 1 | 1 | 1 | 1 |
| Temp. (°C.) | 60–70 | 20–30 | 50–60 | 20–25 |
| Isomerization | | | | |
| Time (hr.) | 5 | 4 | 4 | 4 |
| Temp. (°C.) | 160–165 | 140–150 | 160–165 | 145–150 |
| Crude oily product | | | | |
| Amount (g) | 140 | 142 | 283 | 512 |
| Formula (weight %) | 33 | 49 | 34 | 35 |
| Object comp. | 15 | 10 | 14 | 19 |
| DCB | 15 | 10 | 14 | 19 |
| MBCB | 32 | 23 | 32 | 34 |
| DBCB | 20 | 18 | 20 | 12 |
| Initial distillate (g) | 20 | 14 | 38 | 87 |
| Main distillate (g) | | | | |
| Object compound | 32 | 50 | 65 | 104 |
| filtrate | 59 | 49 | 125 | 219 |
| Last distillate (g) | 23 | 25 | 50 | 77 |

TABLE 3-2

| | Reaction in steady site | | | |
|---|---|---|---|---|
| Test No. | 8 | 9 | 10 | 11 |
| Raw material DCB | | | | |
| Cl site     m- | — | 35 | 3 | 52 |
| Amount (g)  p- | 13 | — | 12 | 22 |
| Recycling material (g) | 80 | 94 | 78 | 417 |
| Al halide | | | | |
| Type | AlCl$_3$ | AlCl$_3$ | AlCl$_3$ | AlCl$_3$ |
| Initial amount (g) | 2 | 2 | 2 | 10 |
| + | + | + | + | + |
| Additional amount (g) | 20 | 20 | 20 | 110 |
| Condition of Reaction | | | | |
| Br addition | | | | |
| Amount (g) | 13.5 | 30 | 15 | 73 |
| Time (hr.) | 0.5 | 0.5 | 0.5 | 1 |
| Temp. (°C.) | 40–50 | 20–30 | 45–55 | 20–25 |
| Isomerization | | | | |
| Time (hr.) | 4.5 | 3.5 | 4.5 | 4 |
| Temp. (°C.) | 160–165 | 140–150 | 155–160 | 145–150 |
| Crude oily product | | | | |
| Amount Formula (weight %) | 97 | 141 | 98 | 520 |
| Object comp. | 30 | 42 | 31 | 29 |
| DCB | 23 | 10 | 23 | 20 |
| MBCB | 36 | 30 | 35 | 35 |
| DBCB | 11 | 18 | 11 | 16 |
| Initial distillate (g) | 24 | 15 | 23 | 101 |
| Main distillate (g) | | | | |
| Object compound | 16 | 45 | 19 | 88 |
| filtrate | 45 | 53 | 44 | 239 |
| Last distillate (g) | 10 | 26 | 10 | 84 |

EXAMPLE 4

Production of 1-bromo-3,5-dichlorobenzene from dichlorobenzene

The first reaction of Example 3 was repeated except adding all of the aluminum halide before the addition of bromine. The object compound was separated from the resulting crude oily product and a part or all of the residue was recycled in the second reaction. The results are shown in Table 4-1 and Table 4-2.

TABLE 4-1

| | | First Reaction | | |
|---|---|---|---|---|
| Test No. | | 12 | 13 | 14 |
| Raw material DCB | | | | |
| Cl site | o- | — | 120 | — |
| Amount (g) | m- | 100 | 300 | — |
| | p- | — | 180 | 100 |
| Al halide | | | | |
| Type | | AlCl$_3$ | AlCl$_3$ | AlCl$_3$ |
| Amount (g) | | 15 | 180 | 40 |
| Condition of Reaction | | | | |
| Br addition | | | | |
| Amount (g) | | 54.4 | 320 | 109 |
| Time (hr.) | | 1 | 1 | 1 |
| Temp. (°C.) | | room temp. | 25–30 | 40 |
| Isomerization | | | | |
| Addition of m-DCB | | — | — | 100 |
| Time (hr.) | | 3 | 8 | 10 |
| Temp. (°C.) | | 150 | 170 | 150–160 |
| Crude oily product | | | | |
| Amount (g) | | 123 | 715 | 250 |
| Formula (weight %) | | | | |
| Object comp. | | 41 | 26 | 37 |
| DCB | | 40 | 42 | 39 |
| MBCB | | 19 | 30 | 22 |
| DBCB | | tr. | 3 | 2 |
| Initial distillate (g) | | 48 | 293 | 100 |
| Main distillate | | | | |
| Object compound (g) | | 34 | 96 | 62 |
| filtrate (g) | | 40 | 287 | 85 |

TABLE 4-2

| | | Second Reaction | | |
|---|---|---|---|---|
| Test No. | | 12 | 13 | 14 |
| Raw material DCB | | | | |
| Cl site | o- | — | 24.4 | — |
| Amount (g) | m- | 70 | 61 | 75 |
| | p- | — | 36.6 | — |
| Recycling material | | | | |
| Type | | filtrate | whole residue | part filtrate |
| Amount (g) | | 40 | 580 | 38 |
| Al halide | | | | |
| Type | | AlCl$_3$ | AlCl$_3$ | AlCl$_3$ |
| Amount (g) | | 15 | 180 | 15 |
| Condition of Reaction | | | | |
| Br addition | | | | |
| Amount (g) | | 27.2 | 124 | 27.2 |
| Time (hr.) | | 0.5 | 0.5 | 0.5 |

TABLE 4-2-continued

| | Second Reaction | | |
|---|---|---|---|
| Test No. | 12 | 13 | 14 |
| Temp. (°C.) | room temp. | 25-30 | room temp. |
| Isomerization | | | |
| Time (hr.) | 3.5 | 8 | 4.5 |
| Temp. (°C.) | 150 | 170 | 150 |
| Crude oily product | | | |
| Amount (g) | 125 | 721 | 120 |
| Formula (weight %) | | | |
| Object compound | 41 | 26 | 39 |
| DCB | 40 | 42 | 41 |
| MBCB | 19 | 30 | 20 |
| DBCB | tr. | 2 | tr. |
| Initial distillate (g) | 50 | 266 | 51 |
| Main distillate (g) | | | |
| Object compound | 29 | 100 | 29 |
| filtrate | 44 | 311 | 38 |

EXAMPLE 5

Production of 1-bromo-3,5-dichlorobenzene from dichlorobenzene

The first reaction of Example 4 was repeated except charging anhydrous aluminum bromide into metadichlorobenzene and adding bromine after heating it to the temperature for isomerization so as to perform both of the bromination and the isomerization at the same time. The results are shown in Table 5-1.

The whole of the residue of the filtrate, the initial distillate and the last distillate was recycled to mix it with the fresh raw material and the second reaction was carried out and the operation was repeated. The results in the steady state are shown in Table 5-2.

TABLE 5-1

| First Reaction | |
|---|---|
| Test No. | 15 |
| Raw material DCB | |
| Cl site | m- |
| Amount (g) | 100 |
| Aluminum bromide (g) | 32 |
| Condition of Reaction | |
| Br addition | |
| Amount (g) | 98 |
| Time (hr.) | 1 |
| Temperature (°C.) | 150 |
| Total Reaction Time (hr.) | 6 |
| Crude oily product | |
| Amount (g) | 147 |
| Formula (weight %) | |
| Object compound | 45 |
| DCB | 15 |
| MBCB | 25 |
| DBCB | 15 |
| Initial distillate (g) | 23 |
| Main distillate | |
| Object compound (g) | 53 |
| filtrate (g) | 48 |
| Last distillate (g) | 21 |

TABLE 5-2

| Reaction in steady site | |
|---|---|
| Test No. | 15 |
| Raw material DCB | |
| Cl site | m- |
| Amount (g) | 38 |
| Recycling material (g) | 92 |
| Aluminum bromide (g) | 32 |
| Condition of Reaction | |
| Br addition | |
| Amount (g) | 38 |

TABLE 5-2-continued

| Reaction in steady site | |
|---|---|
| Test No. | 15 |
| Time (hr.) | 0.5 |
| Temperature (°C.) | 150 |
| Total Reaction Time (hr.) | 6 |
| Crude oily product | |
| Amount (g) | 148 |
| Formula (weight %) | |
| Object compound | 44 |
| DCB | 15 |
| MBCB | 26 |
| DBCB | 15 |
| Initial distillate (g) | 22 |
| Main distillate (g) | |
| Object compound | 51 |
| filtrate | 51 |
| Last distillate 20 | |

What is claimed is:

1. A process for producing 1-bromo-3,5-dichlorobenzene which comprises;
    (a) brominating m-dichlorobenzene, p-dichlorobenzene or a mixture of dichlorobenzene compounds not including more than 20% by weight of o-dichlorobenzene by adding bromine to the dichlorobenzene compound at 0° to 180° C. in the presence of an aluminum halide at a mole ratio of 0.001 to 1 of aluminum halide to total amount of halobenzenes thereby obtaining product bromodichlorobenzene compounds;
    (b) isomerizing the product bromodichlorobenzene compounds in the reaction mixture at 80° to 180° C. in the presence of an aluminum halide at a mole ratio of 0.02 to 1 of aluminum halide to total amount of halobenzenes after the bromination reaction thereby forming a product mixture comprising (a) monobromodichlorobenzene, (b) dichlorobenzene, and (c) dibromodichlorobenzene;
    (c) distilling the reaction mixture to separate the dichlorobenzene, the monobromodichlorobenzene and the dibromodichlorobenzene components from the reaction mixture;
    (d) cooling the monobromodichlorobenzene thereby crystallizing 1-bromo-3,5-dichlorobenzene and separating the same; and
    (e) recycling a portion or all of the residue constituting dichlorobenzene, dibromodichlorobenzene and the monobromodichlorobenzene not containing substantial amounts of 1-bromo-3,5-dichlorobenzene into a fresh raw material for said bromination reaction of step (a) or into the bromination product of step (b) which is to be isomerized.

2. The process of claim 1, wherein the aluminum halide is anhydrous aluminum chloride.

3. The process of claim 1, wherein the addition of bromine is carried out at 0° to 70° C. in the presence of an aluminum halide at a mole ratio of 0.005 to 0.1 to total amount of halobenzenes; and the isomerization is performed by adding an additional amount of aluminum halide to the reaction product so as to give a mole ratio of 0.1 to 0.5 of aluminum halide to the total amount of halobenzenes and heating the reaction product at 120° to 170° C.

4. The process of claim 1, wherein the addition of bromine is carried out at 0° to 70° C. in the presence of an aluminum halide at a mole ratio of 0.1 to 0.5 of aluminum halide to the total amount of halobenzenes; and isomerizing said bromo-dichlorobenzenes by heating the reaction product at 120° C. to 170° C. after the addition of bromine to the reaction product.

5. The process of claim 1, wherein the addition of bromine is carried out at 120° to 170° C. in the presence of an aluminum halide at a mole ratio of 0.1 to 0.5 of aluminum halide to total amount of halobenzenes whereby the bromination and the isomerization reactions are performed in parallel.

6. The process of claim 1, wherein said bromination and isomerization reactions are conducted simultaneously by adding bromine to said halobenzenes at 120° C. to 170° C. in the presence of aluminum halide at a mole ratio of 0.1 to 0.5 of aluminum halide to the total amount of halobenzenes present.

7. The process of claim 1, wherein the process further comprises:
  brominating m-dichlorobenzene with bromine at 0° to 170° C. in the presence of an aluminum halide at a mole ratio of 0.001 to 1 to total amount of halobenzenes thereby preparing a product containing a substantial amount of 1-bromo-2,4-dichlorobenzene; and
  isomerizing said 1-bromo-2,4-dichlorobenzene in said product at 80° to 170° C. in the presence of an aluminum halide at a mole ratio of aluminum halide to total amount of halobenzenes of 0.02 to 1.0 after the bromination reaction.

8. The process of claim 1, wherein the isomerization reaction is conducted by isomerizing a mixture of (a) mono-bromo-dichlorobenzene not containing substantial amounts of -bromo-3,5-dichlorobenzene and not including more than 20% by weight of 1-bromo-3,4-dichlorobenzene, (b) dichlorobenzenes, and (c) dibromodichlorobenzene.

* * * * *